United States Patent
Smith

(10) Patent No.: US 12,170,131 B2
(45) Date of Patent: Dec. 17, 2024

(54) SYSTEM FOR DETERMINING CLINICAL TRIAL PARTICIPATION

(71) Applicant: Acclinate Inc., Birmingham, AL (US)

(72) Inventor: Delmonize A. Smith, Birmingham, AL (US)

(73) Assignee: Acclinate Inc., Birmingham, AL (US)

( * ) Notice: Subject to any disclaimer, the term of this patent is extended or adjusted under 35 U.S.C. 154(b) by 356 days.

(21) Appl. No.: 17/824,838

(22) Filed: May 25, 2022

(65) Prior Publication Data

US 2023/0386619 A1 Nov. 30, 2023

(51) Int. Cl.
*G16H 10/20* (2018.01)
*G06Q 50/00* (2012.01)
*G16H 10/60* (2018.01)

(52) U.S. Cl.
CPC ............ *G16H 10/20* (2018.01); *G06Q 50/01* (2013.01); *G16H 10/60* (2018.01)

(58) Field of Classification Search
CPC ........ G16H 10/60; G16H 50/70; G16H 20/10; G16H 10/20; G16H 20/00; G16H 80/00
See application file for complete search history.

(56) References Cited

U.S. PATENT DOCUMENTS

| | | | |
|---|---|---|---|
| 7,251,609 B1 | 7/2007 | McAlindon et al. | |
| 7,415,447 B2 | 8/2008 | Shiffman et al. | |
| 8,731,961 B2 | 5/2014 | Hanina et al. | |
| 9,131,843 B2 | 9/2015 | Myr | |
| 10,496,796 B2 | 12/2019 | Hanina et al. | |
| 11,636,500 B1 * | 4/2023 | Jain | G06Q 30/0203 705/7.32 |
| 2004/0010418 A1 | 1/2004 | Buonocore et al. | |
| 2013/0080186 A1 | 3/2013 | Marks et al. | |
| 2014/0222444 A1 | 8/2014 | Cerello et al. | |
| 2018/0182470 A1 | 6/2018 | Kalathil | |
| 2020/0243167 A1 * | 7/2020 | Will | G06N 20/20 |

\* cited by examiner

*Primary Examiner* — Joseph D Burgess

(74) *Attorney, Agent, or Firm* — BEKIARES ELIEZER LLP

(57) ABSTRACT

A system for prediction of clinical trial participation. The system includes: a processor of a participation probability node; a memory on which are stored machine-readable instructions that when executed by the processor, cause the processor to: receive a clinical trial (CT) request from a user device, parse the CT request to derive at least one CT parameter, query a patients' database based on the at least one CT parameter to store a set of potential CT participants, collect social media activity-related data for each of the potential CT participants from the set, generate a plurality of feature vectors based on the social media activity-related data of the potential CT participants, and provide the feature vectors to the machine learning module for generating a predictive model indicating a participation probability index for each of the potential CT participants.

20 Claims, 7 Drawing Sheets

SYSTEM FOR DETERMINING CLINICAL TRIAL PARTICIPATION

FIELD OF DISCLOSURE

The present disclosure generally relates to clinical trials, and more particularly, to an intelligent AI-based automated system for determination of clinical trial participation by patients.

BACKGROUND

Clinical trials are research studies involving human trial participants for evaluation of safety and efficacy of medical devices and drugs that have been newly developed to treat diseases and health conditions. Clinical trials are typically conducted after the medical device or drug has been tested on animals. Clinical trials typically develop the evidence upon which governmental regulatory agencies rely when approving a medical device or drug for human use.

Clinical trials follow strict scientific standards in order to produce reliable results. The accuracy of the clinical trial results depends on selecting a representative control group of participants who have a disease, ailment or health condition which the new medical device or drug has been developed to treat. In cases where the medical devices and drugs are intended to be effective across a broad spectrum of the human population, for example a measles vaccine, the control group selected for the clinical trial may represent a broad portion of the population. However, a disease, ailment or health condition may afflict only a limited group of the general population, due to the specific etiological and health conditions of that group of patients.

As such, it is critically important to select clinical trial participants which are representative of the afflicted group of patients. For example, the participants may be required to have specific characteristics of age, gender, ethnicity, diagnosis, allergies, pre-existing and other related medical conditions, and the like. Accordingly, a newly developed drug or medical device may be tested by a control group which is comparable to the same general population group to which drug or medical device is intended to be applied. Without performing the clinical trial on the relevant control group of patients, the results of the clinical trial will not be reliable.

Identifying suitable participants for a reliable clinical trial and obtaining their participation in a clinical trial are significant problems in designing a clinical trial. Information describing the medical condition of patients is protected from disclosure by patient privacy and confidentiality laws and regulations, and these laws and regulations prohibit the disclosure of most of the important and relevant information without the consent of the patient. Yet without access to the protected patient medical information, it is difficult to locate and identify suitable participants. When the number of suitable participants is not readily determinable, it is particularly difficult to design a reliable clinical trial that can be successfully concluded.

Conventionally, a comprehensive database of patients and their medical conditions which can be efficiently and lawfully accessed to identify the most relevant clinical trial participants and/or to design the clinical trial may be used. However, there is no way to predict which one of the patients would be likely to agree to participate in trial. Sending thousands of participation requests and waiting for the responses is inefficient and often unpredictable. This may stand in the way of designing the trial, acquiring funding and scheduling trial dates or trial milestones, because it is not known if a sufficient number of the participants will be recruited.

Accordingly, a system and method for an intelligent AI-based automated determination of clinical trial participation are desired.

BRIEF OVERVIEW

This brief overview is provided to introduce a selection of concepts in a simplified form that are further described below in the Detailed Description. This brief overview is not intended to identify key features or essential features of the claimed subject matter. Nor is this brief overview intended to be used to limit the claimed subject matter's scope.

One embodiment of the present disclosure provides a system for an intelligent AI-based automated prediction of clinical trial participation. The system includes a processor of a participation probability (PP) node connected to at least one cloud server node over a network configured to host a machine learning (ML) module; a memory on which are stored machine-readable instructions that when executed by the processor, cause the processor to: receive a clinical trial (CT) request from a user device, parse the CT request to derive at least one CT parameter, query a patients' database based on the at least one CT parameter to store a set of potential CT participants on a local database, collect social media activity-related data for each of the potential CT participants from the set, generate a plurality of feature vectors based on the social media activity-related data for each of the potential CT participants, and provide the plurality of feature vectors to the ML module for generating a predictive model indicating a participation probability index (PPI) for each of the potential CT participants.

Another embodiment of the present disclosure provides a method that includes one or more of: receiving, by a participation probability (PP) node, a clinical trial (CT) request from a user device, parsing, by the PP node, the CT request to derive at least one CT parameter, querying, by the PP node, a patients' database based on the at least one CT parameter to store a set of potential CT participants on a local database, collecting, by the PP node, social media activity-related data for each of the potential CT participants from the set, generating, by the PP node, a plurality of feature vectors based on the social media activity-related data for each of the potential CT participants, and providing the plurality of feature vectors to an ML module for generating a predictive model indicating a participation probability index (PPI) for each of the potential CT participants.

Another embodiment of the present disclosure provides a computer-readable medium including instructions for receiving a clinical trial (CT) request from a user device, parsing the CT request to derive at least one CT parameter, querying a patients' database based on the at least one CT parameter to store a set of potential CT participants on a local database, collecting social media activity-related data for each of the potential CT participants from the set, generating a plurality of feature vectors based on the social media activity-related data for each of the potential CT participants, and providing the plurality of feature vectors to an ML module for generating a predictive model indicating a participation probability index (PPI) for each of the potential CT participants.

Both the foregoing brief overview and the following detailed description provide examples and are explanatory only. Accordingly, the foregoing brief overview and the following detailed description should not be considered to be restrictive. Further, features or variations may be provided in addition to those set forth herein. For example, embodiments may be directed to various feature combinations and sub-combinations described in the detailed description.

BRIEF DESCRIPTION OF THE DRAWINGS

The accompanying drawings, which are incorporated in and constitute a part of this disclosure, illustrate various embodiments of the present disclosure. The drawings contain representations of various trademarks and copyrights owned by the Applicant. In addition, the drawings may contain other marks owned by third parties and are being used for illustrative purposes only. All rights to various trademarks and copyrights represented herein, except those belonging to their respective owners, are vested in and the property of the Applicant. The Applicant retains and reserves all rights in its trademarks and copyrights included herein, and grants permission to reproduce the material only in connection with reproduction of the granted patent and for no other purpose.

Furthermore, the drawings may contain text or captions that may explain certain embodiments of the present disclosure. This text is included for illustrative, non-limiting, explanatory purposes of certain embodiments detailed in the present disclosure. In the drawings.

DETAILED DESCRIPTION

Figure 1A:
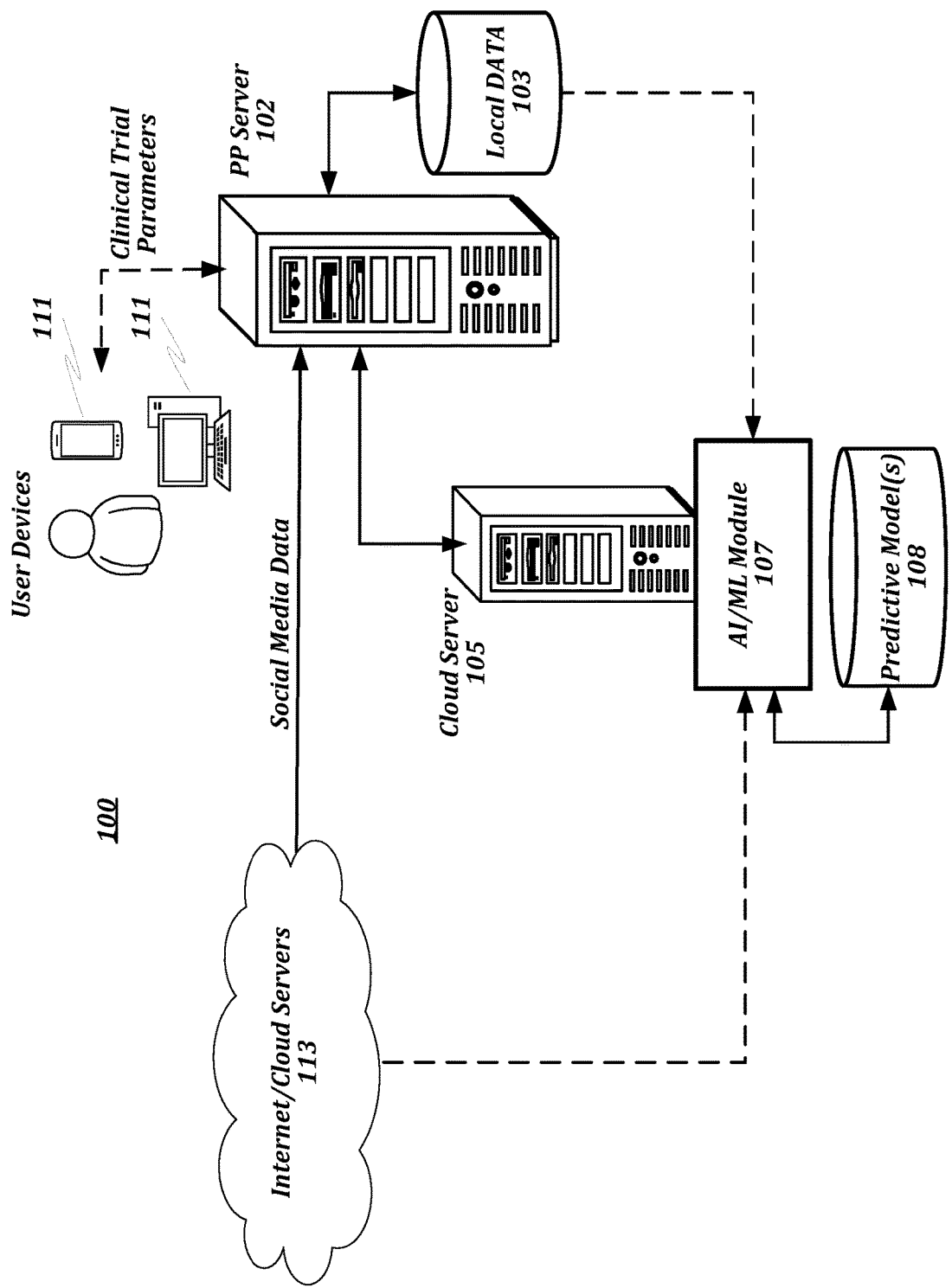
FIG. 1A illustrates a network diagram of a system for an intelligent AI-based automated determination of clinical trial participation consistent with the present disclosure.

As a preliminary matter, it will readily be understood by one having ordinary skill in the relevant art that the present disclosure has broad utility and application. As should be understood, any embodiment may incorporate only one or a plurality of the above-disclosed aspects of the disclosure and may further incorporate only one or a plurality of the above-disclosed features. Furthermore, any embodiment discussed and identified as being "preferred" is considered to be part of a best mode contemplated for carrying out the embodiments of the present disclosure. Other embodiments also may be discussed for additional illustrative purposes in providing a full and enabling disclosure. Moreover, many embodiments, such as adaptations, variations, modifications, and equivalent arrangements, will be implicitly disclosed by the embodiments described herein and fall within the scope of the present disclosure.

Accordingly, while embodiments are described herein in detail in relation to one or more embodiments, it is to be understood that this disclosure is illustrative and exemplary of the present disclosure and are made merely for the purposes of providing a full and enabling disclosure. The detailed disclosure herein of one or more embodiments is not intended, nor is to be construed, to limit the scope of patent protection afforded in any claim of a patent issuing here from, which scope is to be defined by the claims and the equivalents thereof. It is not intended that the scope of patent protection be defined by reading into any claim a limitation found herein that does not explicitly appear in the claim itself.

Thus, for example, any sequence(s) and/or temporal order of steps of various processes or methods that are described herein are illustrative and not restrictive. Accordingly, it should be understood that, although steps of various processes or methods may be shown and described as being in a sequence or temporal order, the steps of any such processes or methods are not limited to being carried out in any particular sequence or order, absent an indication otherwise. Indeed, the steps in such processes or methods generally may be carried out in various different sequences and orders while still falling within the scope of the present invention. Accordingly, it is intended that the scope of patent protection is to be defined by the issued claim(s) rather than the description set forth herein.

Additionally, it is important to note that each term used herein refers to that which an ordinary artisan would understand such term to mean based on the contextual use of such term herein. To the extent that the meaning of a term used herein—as understood by the ordinary artisan based on the contextual use of such term—differs in any way from any particular dictionary definition of such term, it is intended that the meaning of the term as understood by the ordinary artisan should prevail.

Regarding applicability of 35 U.S.C. § 112, ¶6, no claim element is intended to be read in accordance with this statutory provision unless the explicit phrase "means for" or "step for" is actually used in such claim element, whereupon this statutory provision is intended to apply in the interpretation of such claim element.

Furthermore, it is important to note that, as used herein, "a" and "an" each generally denotes "at least one," but does not exclude a plurality unless the contextual use dictates otherwise. When used herein to join a list of items, "or" denotes "at least one of the items," but does not exclude a plurality of items of the list. Finally, when used herein to join a list of items, "and" denotes "all of the items of the list."

The following detailed description refers to the accompanying drawings. Wherever possible, the same reference numbers are used in the drawings and the following description to refer to the same or similar elements. While many embodiments of the disclosure may be described, modifications, adaptations, and other implementations are possible. For example, substitutions, additions, or modifications may be made to the elements illustrated in the drawings, and the methods described herein may be modified by substituting, reordering, or adding stages to the disclosed methods. Accordingly, the following detailed description does not limit the disclosure. Instead, the proper scope of the disclosure is defined by the appended claims. The present disclosure contains headers. It should be understood that these headers are used as references and are not to be construed as limiting upon the subjected matter disclosed under the header.

The present disclosure includes many aspects and features. Moreover, while many aspects and features relate to, and are described in, the context of processing job applicants, embodiments of the present disclosure are not limited to use only in this context.

The present disclosure provides a system, method and computer-readable medium for an intelligent AI-based automated determination of clinical trial participation.

In one embodiment of the present disclosure, the system provides for AI and machine learning (ML)-generated list of potential clinical trial participants with a high degree of participation probability. An automated decision model may be configured to provide for identification of the most likely clinical trial participants based on a correspondence between clinical trial parameters and data acquired from social media of the potential participants.

For example, a trial organizer may provide clinical trial parameters such as age range of participants, a particular disease or condition or diagnosis, location of the trial, incentives, etc. Then the AI/ML system may determine the most likely clinical trial participants that qualify for the clinical trial based on the clinical trial parameters and may be highly likely to participate based on the social media data. For non-limiting example, the clinical trial is intended for testing a MS-related oral medication. Then, the AI/ML system may be able to identify the MS patients who express interest in taking oral MS medications instead of injectable ones in their social media post in MS forums or groups based on the data collected from the social media of these MS patients.

In one disclosed embodiment, the AI/ML technology may be combined with blockchain technology for secure use of patients' data. The disclosed embodiment may produce a detailed per-patient score on the patient's likelihood to participate in a trial. This allows direct monitoring of a user's trust and can aid in further, more direct method of increasing their levels of trust to enroll them in a trial. Using the above example, an MS patient may be sent specific content related to new oral MS medications. The system may monitor patient's activity with respect to this content. For example, if the patient comments on the content, shares it in the discussion group or reposts it, then the patient may be interested in a future clinical trial of an oral MS medication when it occurs in his or her geographical area. The patient's heuristics may be stored or recorded on a blockchain for training of the AI/ML model. As such, the disclosed embodiment no only determines the patients that are already interested in a clinical trial participation, but also looks into converting patients into future clinical trial participants by modifying their participation probability.

In one embodiment, the system may use an AI and machine learning (ML) to determine the participation probability index (PPI) of an individual in a clinical trial. More specifically, a participation probability (PP) server ingests participant's data from multiple sources, including social media accounts as a primary data source. The PP server then runs the predictive models necessary to know who to ask, when to ask, and how to ask in terms of continued engagement and potential clinical trial participation. The PP server may generate a trial specific index referred to as a Likelihood to Participate (LTP) which may be used to determine when to ask a potential participant to join a clinical trial. An LTP score may be calculated based on potential participant's data such as age, gender, insurance, current medication(s) taken, diagnosis, previous participation history, relevant on-line activity, etc.

The PP server may build a local database of participant leads by querying available medical databases based on one or more clinical trial parameters (e.g., MS medications, etc.) The PP server may provide a specific content (based on medical relevance) to the potential participants to engage the participant via multiple digital channels to expand on participants' profiles and to determine initial PPI score for the potential participants. The PP server may establish a baseline PPI score by ingesting participant profile feature vector data into an AI module. As discussed above, the PP server may track potential participant(s) engagement activity on social media and other media channels to adjust the PPI based on processing the participant's engagement activity data through the AI/ML module. The PP server may segment potential clinical trial participants across low-medium-high PPI scores. The PP server may automatically recommend engagements (i.e., relevant content) to increase the PPI for low-medium participants.

FIG. 1A illustrates a network diagram of a system for an intelligent AI-based automated determination of clinical trial participation consistent with the present disclosure.

Referring to FIG. 1A, the example network 100 includes the participation probability (PP) server node 102 connected to a cloud server node(s) 105 over a network. The cloud server node(s) 105 is configured to host an AI/ML module 107. The PP server node 102 may receive clinical trial parameters from a user device 111 that may be a smartphone, a tablet, a laptop/PC, etc. As discussed above, the PP server node 102 may query available patient databases (not shown) based on the clinical trial parameters and may store the patients' data in a local database 103.

The PP server 102 may establish a baseline PPI score by ingesting participant profile feature vector data into an AI/ML module 107. As discussed above, the PP server 102 may provide a specific content (based on medical relevance) to the potential participants from the local database 103 to engage the participants via multiple digital channels via Internet and/or cloud servers 113 (such as web servers) to expand on participants' profiles and to determine initial PPI score for the potential participants. The PP server 102 may track potential participants' engagement activity on social media and other media channels to adjust the PPI based on processing the participants' engagement activity data through the AI/ML module 107. The PP server 102 may segment potential clinical trial participants across low-medium-high PPA scores. The PP server 102 may automatically recommend engagements (i.e., relevant content) to increase the PPI for low-medium participants. The AI/ML module 107 may generate a predictive model(s) 108 to predict user behavior in response to the specific relevant content based on pre-stored heuristics data collected and stored in the local database 103. This way, the participant participation in the clinical trial may be predicted based not only on the current PPI score, but based on heuristics data of the given potential clinical trial participant. Once the list of the potential participants is established based on a desired LTP score, these participants may be contacted and invited to the clinical trial.

Figure 1B:
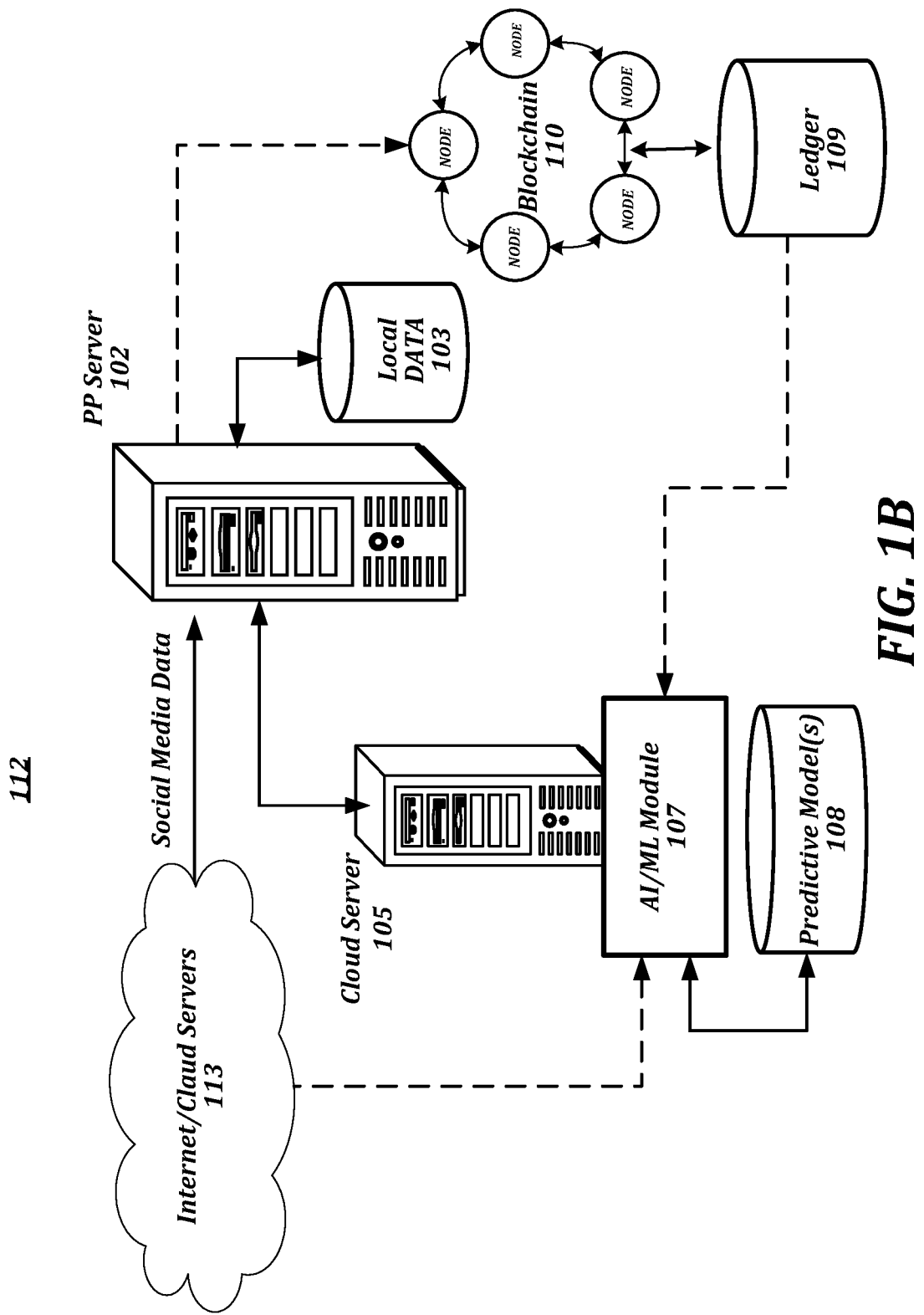
FIG. 1B illustrates a network diagram of a system for an intelligent AI-based automated determination of clinical trial participation using a blockchain consistent with the present disclosure.

FIG. 1B illustrates a network diagram of a system for an intelligent AI-based automated determination of clinical trial participation using a blockchain consistent with the present disclosure.

Referring to FIG. 1B, the example network 112 includes the participation probability (PP) server node 102 connected to a cloud server node(s) 105 over a network. The cloud server node(s) 105 is configured to host an AI/ML module 107. In one embodiment, the AI/ML module 107 may be implemented on the PP server node 102. As discussed above, the PP server node 102 may query available patient databases (not shown) based on the clinical trial parameters received from a trial organizer and may store the patients' data in a local database 103.

The PP server 102 may establish a baseline PPI score by ingesting participant profile feature vector data into an AI/ML module 107. As discussed above, the PP server 102 may provide a specific content (based on medical relevance) to the potential participants from the local database 103 to engage the participants via multiple digital channels via Internet and/or cloud servers 113 (such as web servers) to expand on participants' profiles and to determine initial PPI score for the potential participants. The PP server 102 may track potential participants' engagement activity on social media and other media channels to adjust the PPI based on processing the participants' engagement activity data through the AI/ML module 107.

In one embodiment, the PP server node 102 may receive patients' data including confidential medical data from a database 110 ledger 109 based on a consensus from medical organization or from patients. Additionally, confidential clinical trial-related information may also be acquired from the private blockchain 110. The heuristics data from each step of engagement with the relevant medical content may be also recorded on a private blockchain 110. In this implementation the PP server 102 and the cloud server 105 may server as blockchain 110 peer nodes. The PP server 102 may segment potential clinical trial participants across low-medium-high PPA scores. The PP server 102 may automatically recommend engagements (i.e., relevant content) to increase the PPI for low-medium participants. The AI/ML module 107 may generate a predictive model(s) 108 to predict user behavior in response to the specific relevant content based on pre-stored heuristics data acquired from the blockchain 110. This way, the participant participation in the clinical trial may be predicted based not only on the current PPI score, but based on the previously collected heuristics data of the given potential clinical trial participant. Once the list of the potential participants is established based on a desired LTP score, these participants may be contacted and invited to the clinical trial.

As discussed above, the AI/ML module 107 may provide predictive outputs data that indicate the LTP scores of the potential clinical trial participants. The PP server node 102 may process the predictive outputs data received from the AI/ML module 107 to generate a reliable list of the potential clinical trial participants.

Figure 2:
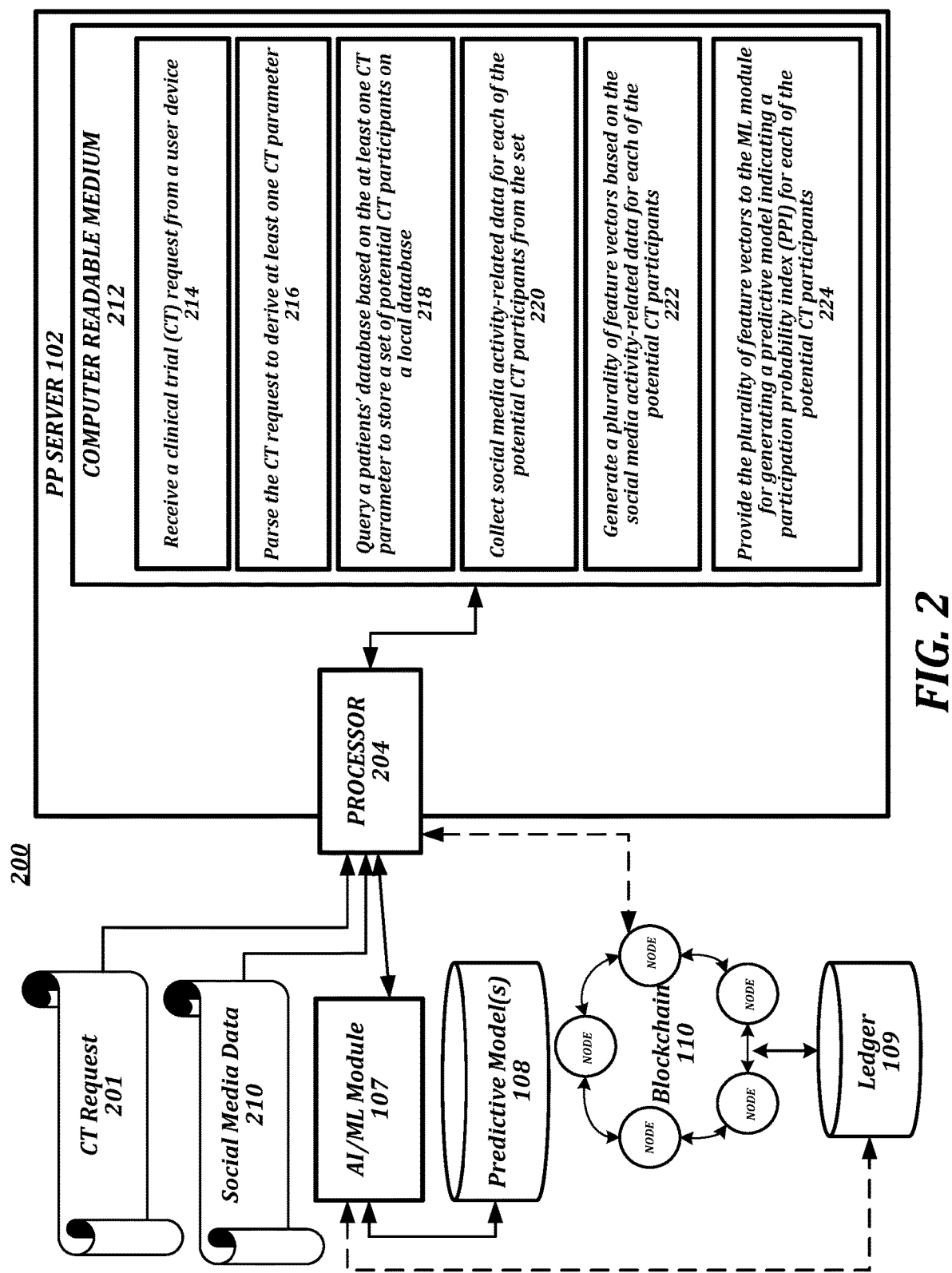
FIG. 2 illustrates a network diagram of a system including detailed features of a participation prediction server node consistent with the present disclosure.

FIG. 2 illustrates a network diagram of a system including detailed features of a participation prediction (PP) server node 102 consistent with the present disclosure.

Referring to FIG. 2, the example network 200 includes the PP server node 102 connected to a cloud server node(s) 105 over a network. The cloud server node(s) 105 is configured to host an AI/ML module 107. As discussed above with reference to FIGS. 1A-B, the PP server node 102 may receive clinical trial parameters data 201.

The AI/ML module 107 may generate a predictive model (s) 108 based on historical trial participation-related data provided by the PP server 102 from a local data storage or from a permissioned blockchain 110 ledger 109 based on the trial parameters data 201. The trial parameters data may be recorded on a permissioned blockchain 110 ledger 109. As discussed above, the AI/ML module 107 may provide predictive outputs data that indicate trial participation based on the trial parameters and heretics data acquired form the ledger 109. Note that the AI/ML module 107 may be implemented on the PP server node 102. The PP server node 102 may process the predictive outputs data received from the AI/ML module 107 to generate a list of clinical trial participants.

While this example describes in detail only one PP server node 102, multiple such nodes may be connected to the network and to the blockchain 110. It should be understood that the PP server node 102 may include additional components and that some of the components described herein may be removed and/or modified without departing from a scope of the PP server node 102 disclosed herein. The PP server node 102 may be a computing device or a server computer, or the like, and may include a processor 204, which may be a semiconductor-based microprocessor, a central processing unit (CPU), an application specific integrated circuit (ASIC), a field-programmable gate array (FPGA), and/or another hardware device. Although a single processor 204 is depicted, it should be understood that the PP server node 102 may include multiple processors, multiple cores, or the like, without departing from the scope of the PP server node 102 system.

The PP server node 102 may also include a non-transitory computer readable medium 212 that may have stored thereon machine-readable instructions executable by the processor 205. Examples of the machine-readable instructions are shown as 214-224 and are further discussed below. Examples of the non-transitory computer readable medium 212 may include an electronic, magnetic, optical, or other physical storage device that contains or stores executable instructions. For example, the non-transitory computer readable medium 212 may be a Random-Access memory (RAM), an Electrically Erasable Programmable Read-Only Memory (EEPROM), a hard disk, an optical disc, or other type of storage device.

The processor 204 may fetch, decode, and execute the machine-readable instructions 214 to receive a clinical trial (CT) request from a user device 111. The processor 204 may fetch, decode, and execute the machine-readable instructions 216 to parse the CT request 201 to derive at least one CT parameter. The processor 204 may fetch, decode, and execute the machine-readable instructions 218 to query a patients' database based on the at least one CT parameter to store a set of potential CT participants on a local database 103. The processor 204 may fetch, decode, and execute the machine-readable instructions 220 to collect social media activity-related data for each of the potential CT participants from the set.

The processor 204 may fetch, decode, and execute the machine-readable instructions 222 to generate a plurality of feature vectors based on the social media activity-related data 210 for each of the potential CT participants. The processor 204 may fetch, decode, and execute the machine-readable instructions 224 to provide the plurality of feature vectors to the ML module 107 for generating a predictive model 108 indicating a participation probability index (PPI) for each of the potential CT participants. The permissioned blockchain 110 may be configured to use one or more smart contracts that manage transactions for multiple participating nodes and for recording the transactions on the ledger 109.

Figure 3A:
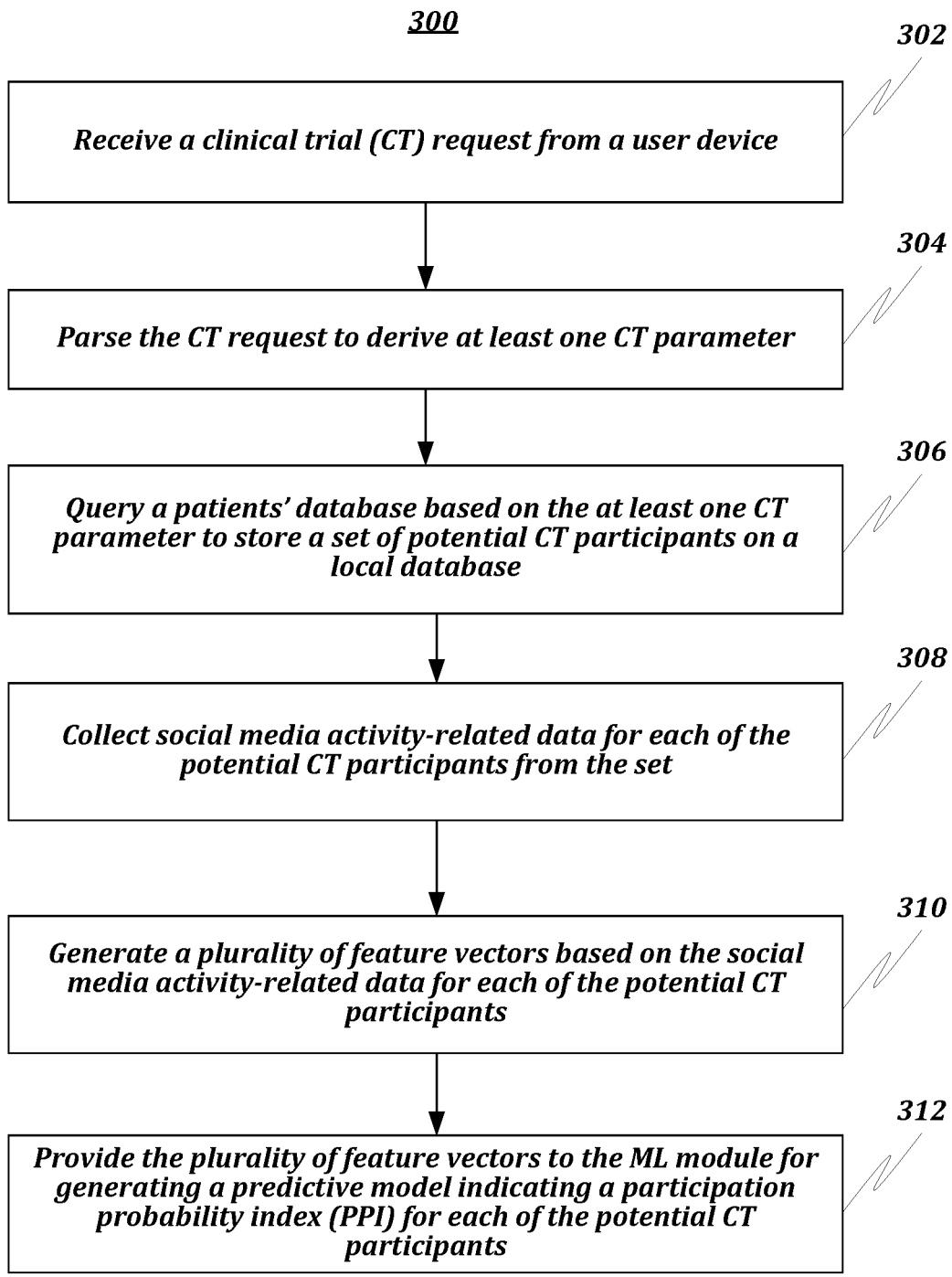
FIG. 3A illustrates a flowchart of a method for an intelligent AI-based automated determination of clinical trial participation consistent with the present disclosure.

FIG. 3A illustrates a flowchart of a method for an intelligent AI-based prediction of a clinical trial participation consistent with the present disclosure.

Referring to FIG. 3A, the method 300 may include one or more of the steps described below. FIG. 3A illustrates a flow chart of an example method executed by the PP server 102

(see FIG. 2). It should be understood that method 300 depicted in FIG. 3A may include additional operations and that some of the operations described therein may be removed and/or modified without departing from the scope of the method 300. The description of the method 300 is also made with reference to the features depicted in FIG. 2 for purposes of illustration. Particularly, the processor 204 of the PP server 102 may execute some or all of the operations included in the method 300.

With reference to FIG. 3A, at block 302, the processor 204 may receive a clinical trial (CT) request from a user device. At block 304, the processor 204 may parse the CT request to derive at least one CT parameter. At block 306, the processor 204 may query a patients' database based on the at least one CT parameter to store a set of potential CT participants on a local database. At block 308, the processor 204 may collect social media activity-related data for each of the potential CT participants from the set. At block 310, the processor 204 may generate a plurality of feature vectors based on the social media activity-related data for each of the potential CT participants. At block 312, the processor 204 may provide the plurality of feature vectors to the ML module for generating a predictive model indicating a participation probability index (PPI) for each of the potential CT participants.

Figure 3B:
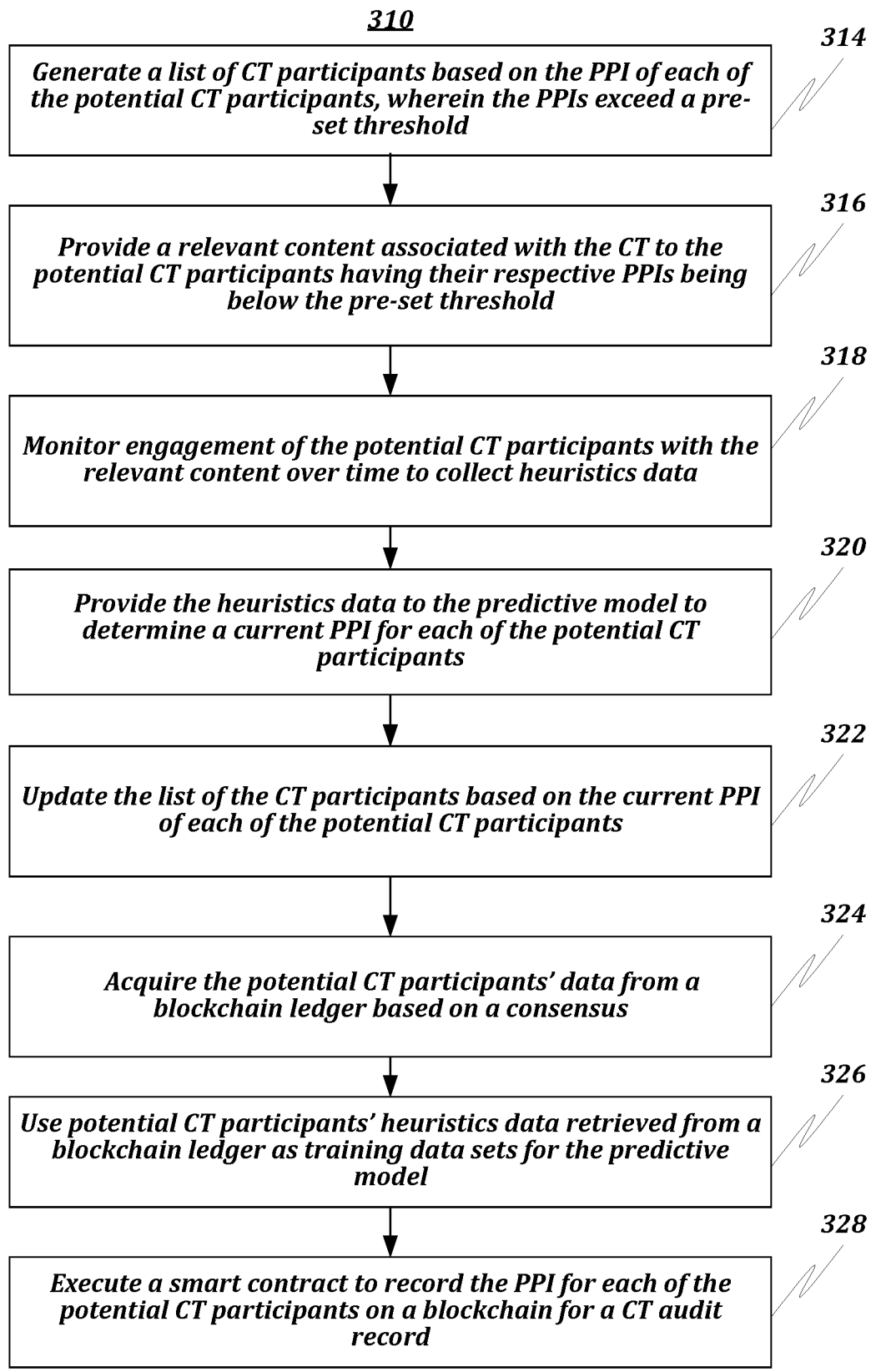
FIG. 3B illustrates a further flow chart of a method for the intelligent AI-based automated determination of clinical trial participation consistent with the present disclosure.

FIG. 3B illustrates a further flowchart of a method for an automated AI-based determination of clinical trial participation consistent with the present disclosure. Referring to FIG. 3B, the method 310 may include one or more of the steps described below. FIG. 3B illustrates a flow chart of an example method executed by the PP server 102 (see FIG. 2). It should be understood that method 310 depicted in FIG. 3B may include additional operations and that some of the operations described therein may be removed and/or modified without departing from the scope of the method 310. The description of the method 310 is also made with reference to the features depicted in FIG. 2 for purposes of illustration. Particularly, the processor 204 of the PP server 102 may execute some or all of the operations included in the method 300.

With reference to FIG. 3B, at block 314, the processor 204 may generate a list of clinical trial (CT) participants based on the PPI of each of the potential CT participants, wherein the PPIs exceed a pre-set threshold. At block 316, the processor 204 may provide a relevant content associated with the CT to the potential CT participants having their respective PPIs being below the pre-set threshold. At block 318, the processor 204 may monitor engagement of the potential CT participants with the relevant content over time to collect heuristics data. At block 320, the processor 204 may provide the heuristics data to the predictive model to determine a current PPI for each of the potential CT participants. At block 322, the processor 204 may update the list of the CT participants based on the current PPI of each of the potential CT participants. At block 324, the processor 204 may acquire the potential CT participants' data from a blockchain ledger based on a consensus. At block 326, the processor 204 may use potential CT participants' heuristics data retrieved from a blockchain ledger as training data sets for the predictive model. At block 328, the processor 204 may execute a smart contract to record the PPI for each of the potential CT participants on a blockchain for a CT audit record.

In one disclosed embodiment, the clinical trial participation model may be generated by an AI/ML module 107 that may use training data sets to improve accuracy of the prediction of trial participation. The parameters used in training data sets may be stored in a centralized database 103 (FIG. 1A). In one embodiment, a neural network may be used for trial participation modeling and prediction.

In another embodiment, the AI/ML module 107 may use a decentralized storage such as a blockchain 110 (see FIG. 1B) that is a distributed storage system, which includes multiple nodes that communicate with each other. The decentralized storage includes an append-only immutable data structure resembling a distributed ledger capable of maintaining records between mutually untrusted parties. The untrusted parties are referred to herein as peers or peer nodes. Each peer maintains a copy of the parameter(s) records and no single peer can modify the records without a consensus being reached among the distributed peers. For example, the peers may execute a consensus protocol to validate blockchain storage transactions, group the storage transactions into blocks, and build a hash chain over the blocks. This process forms the ledger by ordering the storage transactions, as is necessary, for consistency. In various embodiments, a permissioned and/or a permissionless blockchain can be used. In a public or permissionless blockchain, anyone can participate without a specific identity. Public blockchains can involve assets and use consensus based on various protocols such as Proof of Work (PoW). On the other hand, a permissioned blockchain provides secure interactions among a group of entities which share a common goal such as donating and collecting funds for a common charitable cause, but which do not fully trust one another.

This application can utilize a permissioned (private) blockchain that operates arbitrary, programmable logic, tailored to a decentralized storage scheme and referred to as "smart contracts" or "chaincodes." In some cases, specialized chaincodes may exist for management functions and parameters which are referred to as system chaincodes. The application can further utilize smart contracts that are trusted distributed applications which leverage tamper-proof properties of the blockchain database and an underlying agreement between nodes, which is referred to as an endorsement or endorsement policy. Blockchain transactions associated with this application can be "endorsed" before being committed to the blockchain while transactions, which are not endorsed, are disregarded. An endorsement policy allows chaincodes to specify endorsers for a transaction in the form of a set of peer nodes that are necessary for endorsement. When a client sends the transaction to the peers specified in the endorsement policy, the transaction is executed to validate the transaction. After a validation, the transactions enter an ordering phase in which a consensus protocol is used to produce an ordered sequence of endorsed transactions grouped into blocks.

Figure 4:
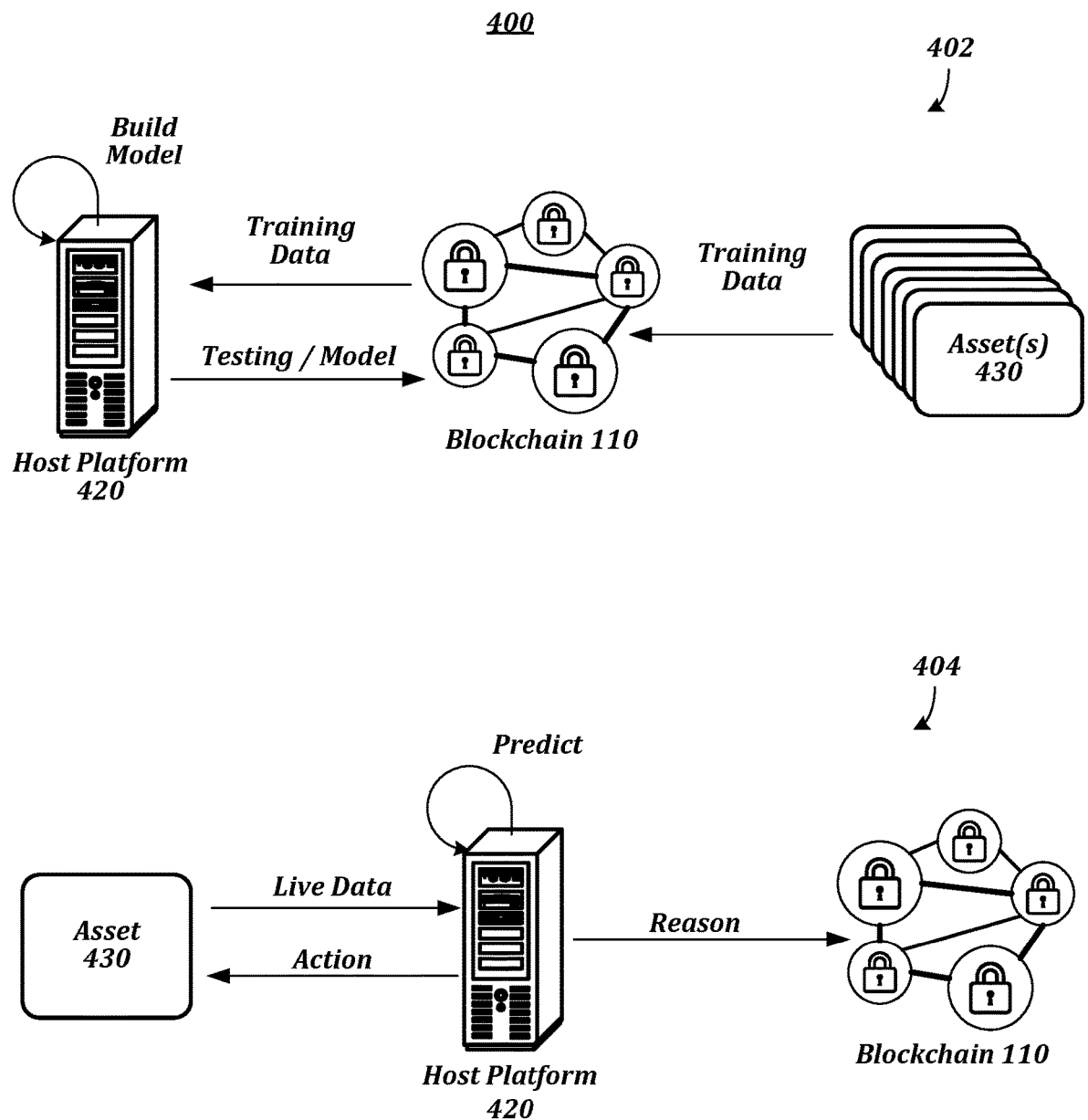
FIG. 4 illustrates deployment of a machine learning model for predictive monitoring of blockchain assets consistent with the present disclosure.

In the example depicted in FIG. 4, a host platform 420 builds and deploys a machine learning model for predictive monitoring of assets 430. Here, the host platform 520 may be a cloud platform, an industrial server, a web server, a personal computer, a user device, and the like. Assets 430 can represent patients' parameters. The blockchain 110 can be used to significantly improve both a training process 402 of the machine learning model and a clinical trial participation predictive process 405 based on a trained machine learning model. For example, in 402, rather than requiring a data scientist/engineer or other user to collect the data, historical (heuristics) data may be stored by the assets 430 themselves (or through an intermediary, not shown) on the blockchain 110.

This can significantly reduce the collection time needed by the host platform 420 when performing predictive model training. For example, using smart contracts, data can be directly and reliably transferred straight from its place of origin (e.g., from patients' social media) to the blockchain 110. By using the blockchain 110 to ensure the security and ownership of the collected data, smart contracts may directly send the data from the assets to the entities that use the data for building a machine learning model. This allows for sharing of data among the assets 430. The collected data may be stored in the blockchain 110 based on a consensus mechanism. The consensus mechanism pulls in (permissioned nodes) to ensure that the data being recorded is verified and accurate. The data recorded is time-stamped, cryptographically signed, and immutable. It is therefore auditable, transparent, and secure.

Furthermore, training of the machine learning model on the collected data may take rounds of refinement and testing by the host platform 420. Each round may be based on additional data or data that was not previously considered to help expand the knowledge of the machine learning model. In 402, the different training and testing steps (and the data associated therewith) may be stored on the blockchain 110 by the host platform 420. Each refinement of the machine learning model (e.g., changes in variables, weights, etc.) may be stored on the blockchain 110. This provides verifiable proof of how the model was trained and what data was used to train the model. Furthermore, when the host platform 420 has achieved a finally trained model, the resulting model may be stored on the blockchain 110.

After the model has been trained, it may be deployed to a live environment where it can make clinical trial participation predictions/decisions based on the execution of the final trained machine learning model. In this example, data fed back from the asset 430 may be input into the machine learning model and may be used to make event predictions such as likelihood of participation in the clinical trial. Determinations made by the execution of the machine learning model (e.g., PPI/LTP scores, etc.) at the host platform 420 may be stored on the blockchain 110 to provide auditable/verifiable proof. As one non-limiting example, the machine learning model may predict a future change of a part of the asset 430 (the PPI/LTP score) and create alert or a notification to regenerate a clinical trial participation list. The data behind this decision may be stored by the host platform 420 on the blockchain 110. In one embodiment the features and/or the actions described and/or depicted herein can occur on or with respect to the blockchain 110.

The above embodiments of the present disclosure may be implemented in hardware, in a computer-readable instructions executed by a processor, in firmware, or in a combination of the above. The computer computer-readable instructions may be embodied on a computer-readable medium, such as a storage medium. For example, the computer computer-readable instructions may reside in random access memory ("RAM"), flash memory, read-only memory ("ROM"), erasable programmable read-only memory ("EPROM"), electrically erasable programmable read-only memory ("EEPROM"), registers, hard disk, a removable disk, a compact disk read-only memory ("CD-ROM"), or any other form of storage medium known in the art.

An exemplary storage medium may be coupled to the processor such that the processor may read information from, and write information to, the storage medium. In the alternative, the storage medium may be integral to the processor. The processor and the storage medium may reside in an application specific integrated circuit ("ASIC"). In the alternative embodiment, the processor and the storage medium may reside as discrete components. For example, FIG. 5 illustrates an example computing device (e.g., a server node) 500, which may represent or be integrated in any of the above-described components, etc.

Figure 5:
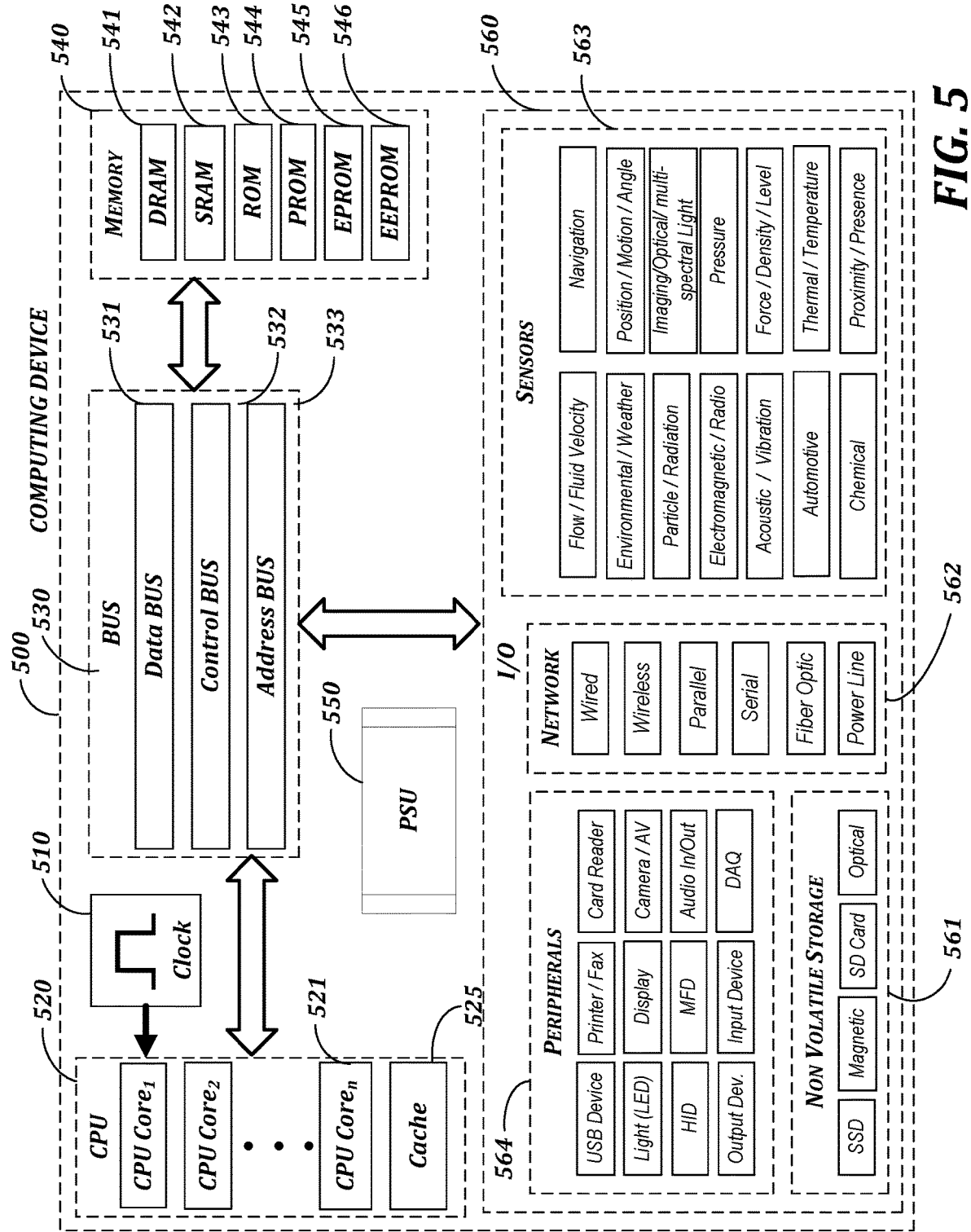
FIG. 5 illustrates a block diagram of a system including a computing device for performing the method of FIGS. 3A and 3B.

FIG. 5 illustrates a block diagram of a system including computing device 500. The computing device 500 may comprise, but not be limited to the following:

Mobile computing device, such as, but is not limited to, a laptop, a tablet, a smartphone, a drone, a wearable, an embedded device, a handheld device, an Arduino, an industrial device, or a remotely operable recording device;

A supercomputer, an exa-scale supercomputer, a mainframe, or a quantum computer;

A minicomputer, wherein the minicomputer computing device comprises, but is not limited to, an IBM AS500/iSeries/System I, A DEC VAX/PDP, a HP3000, a Honeywell-Bull DPS, a Texas Instruments TI-990, or a Wang Laboratories VS Series;

A microcomputer, wherein the microcomputer computing device comprises, but is not limited to, a server, wherein a server may be rack mounted, a workstation, an industrial device, a raspberry pi, a desktop, or an embedded device;

The participation prediction (PP) server node 102 (see FIG. 2) may be hosted on a centralized server or on a cloud computing service. Although method 300 has been described to be performed by the PP server node 102 implemented on a computing device 500, it should be understood that, in some embodiments, different operations may be performed by a plurality of the computing devices 500 in operative communication at least one network.

Embodiments of the present disclosure may comprise a computing device having a central processing unit (CPU) 520, a bus 530, a memory unit 550, a power supply unit (PSU) 550, and one or more Input/Output (I/O) units. The CPU 520 coupled to the memory unit 550 and the plurality of I/O units 560 via the bus 530, all of which are powered by the PSU 550. It should be understood that, in some embodiments, each disclosed unit may actually be a plurality of such units for the purposes of redundancy, high availability, and/or performance. The combination of the presently disclosed units is configured to perform the stages any method disclosed herein.

Consistent with an embodiment of the disclosure, the aforementioned CPU 520, the bus 530, the memory unit 550, a PSU 550, and the plurality of I/O units 560 may be implemented in a computing device, such as computing device 500. Any suitable combination of hardware, software, or firmware may be used to implement the aforementioned units. For example, the CPU 520, the bus 530, and the memory unit 550 may be implemented with computing device 500 or any of other computing devices 500, in combination with computing device 500. The aforementioned system, device, and components are examples and other systems, devices, and components may comprise the aforementioned CPU 520, the bus 530, the memory unit 550, consistent with embodiments of the disclosure.

At least one computing device 500 may be embodied as any of the computing elements illustrated in all of the attached figures, including the design server node 102 (FIG. 2). A computing device 500 does not need to be electronic, nor even have a CPU 520, nor bus 530, nor memory unit 550. The definition of the computing device 500 to a person having ordinary skill in the art is "A device that computes, especially a programmable [usually] electronic machine that performs high-speed mathematical or logical operations or that assembles, stores, correlates, or otherwise processes information." Any device which processes information qualifies as a computing device 500, especially if the processing is purposeful.

With reference to FIG. 5, a system consistent with an embodiment of the disclosure may include a computing device, such as computing device 500. In a basic configuration, computing device 500 may include at least one clock module 110, at least one CPU 520, at least one bus 530, and at least one memory unit 550, at least one PSU 550, and at least one I/O 560 module, wherein I/O module may be comprised of, but not limited to a non-volatile storage sub-module 561, a communication sub-module 562, a sensors sub-module 563, and a peripherals sub-module 565.

A system consistent with an embodiment of the disclosure the computing device 500 may include the clock module 110 may be known to a person having ordinary skill in the art as a clock generator, which produces clock signals. Clock signal is a particular type of signal that oscillates between a high and a low state and is used like a metronome to coordinate actions of digital circuits. Most integrated circuits (ICs) of sufficient complexity use a clock signal in order to synchronize different parts of the circuit, cycling at a rate slower than the worst-case internal propagation delays. The preeminent example of the aforementioned integrated circuit is the CPU 520, the central component of modern computers, which relies on a clock. The only exceptions are asynchronous circuits such as asynchronous CPUs. The clock 110 can comprise a plurality of embodiments, such as, but not limited to, single-phase clock which transmits all clock signals on effectively 1 wire, two-phase clock which distributes clock signals on two wires, each with non-overlapping pulses, and four-phase clock which distributes clock signals on 5 wires.

Many computing devices 500 use a "clock multiplier" which multiplies a lower frequency external clock to the appropriate clock rate of the CPU 520. This allows the CPU 520 to operate at a much higher frequency than the rest of the computer, which affords performance gains in situations where the CPU 520 does not need to wait on an external factor (like memory 550 or input/output 560). Some embodiments of the clock 110 may include dynamic frequency change, where, the time between clock edges can vary widely from one edge to the next and back again.

A system consistent with an embodiment of the disclosure the computing device 500 may include the CPU unit 520 comprising at least one CPU Core 521. A plurality of CPU cores 521 may comprise identical CPU cores 521, such as, but not limited to, homogeneous multi-core systems. It is also possible for the plurality of CPU cores 521 to comprise different CPU cores 521, such as, but not limited to, heterogeneous multi-core systems, big.LITTLE systems and some AMD accelerated processing units (APU). The CPU unit 520 reads and executes program instructions which may be used across many application domains, for example, but not limited to, general purpose computing, embedded computing, network computing, digital signal processing (DSP), and graphics processing (GPU). The CPU unit 520 may run multiple instructions on separate CPU cores 521 at the same time. The CPU unit 520 may be integrated into at least one of a single integrated circuit die and multiple dies in a single chip package. The single integrated circuit die and multiple dies in a single chip package may contain a plurality of other aspects of the computing device 500, for example, but not limited to, the clock 110, the CPU 520, the bus 530, the memory 550, and I/O 560.

The CPU unit 520 may contain cache 522 such as, but not limited to, a level 1 cache, level 2 cache, level 3 cache or combination thereof. The aforementioned cache 522 may or may not be shared amongst a plurality of CPU cores 521. The cache 522 sharing comprises at least one of message passing and inter-core communication methods may be used for the at least one CPU Core 521 to communicate with the cache 522. The inter-core communication methods may comprise, but not limited to, bus, ring, two-dimensional mesh, and crossbar. The aforementioned CPU unit 520 may employ symmetric multiprocessing (SMP) design.

The plurality of the aforementioned CPU cores 521 may comprise soft microprocessor cores on a single field programmable gate array (FPGA), such as semiconductor intellectual property cores (IP Core). The plurality of CPU cores 521 architecture may be based on at least one of, but not limited to, Complex instruction set computing (CISC), Zero instruction set computing (ZISC), and Reduced instruction set computing (RISC). At least one of the performance-enhancing methods may be employed by the plurality of the CPU cores 521, for example, but not limited to Instruction-level parallelism (ILP) such as, but not limited to, super-scalar pipelining, and Thread-level parallelism (TLP).

Consistent with the embodiments of the present disclosure, the aforementioned computing device 500 may employ a communication system that transfers data between components inside the aforementioned computing device 500, and/or the plurality of computing devices 500. The aforementioned communication system will be known to a person having ordinary skill in the art as a bus 530. The bus 530 may embody internal and/or external plurality of hardware and software components, for example, but not limited to a wire, optical fiber, communication protocols, and any physical arrangement that provides the same logical function as a parallel electrical bus. The bus 530 may comprise at least one of, but not limited to a parallel bus, wherein the parallel bus carry data words in parallel on multiple wires, and a serial bus, wherein the serial bus carry data in bit-serial form. The bus 530 may embody a plurality of topologies, for example, but not limited to, a multidrop/electrical parallel topology, a daisy chain topology, and a connected by switched hubs, such as USB bus. The bus 530 may comprise a plurality of embodiments, for example, but not limited to:

Internal data bus (data bus) 531/Memory bus
Control bus 532
Address bus 533
System Management Bus (SMBus)
Front-Side-Bus (FSB)
External Bus Interface (EBI)
Local bus
Expansion bus
Lightning bus
Controller Area Network (CAN bus)
Camera Link
ExpressCard
Advanced Technology management Attachment (ATA), including embodiments and derivatives such as, but not limited to, Integrated Drive Electronics (IDE)/Enhanced IDE (EIDE), ATA Packet Interface (ATAPI), Ultra-Direct Memory Access (UDMA), Ultra ATA (UATA)/Parallel ATA (PATA)/Serial ATA (SATA), CompactFlash (CF) interface, Consumer Electronics ATA (CE-ATA)/Fiber Attached Technology Adapted (FATA), Advanced Host Controller Interface (AHCI), SATA Express (SATAe)/External SATA (eSATA), including the powered embodiment eSATAp/Mini-SATA (mSATA), and Next Generation Form Factor (NGFF)/M.2.

Small Computer System Interface (SCSI)/Serial Attached SCSI (SAS)
HyperTransport
InfiniBand
RapidIO
Mobile Industry Processor Interface (MIPI)
Coherent Processor Interface (CAPI)
Plug-n-play
Wire
Peripheral Component Interconnect (PCI), including embodiments such as, but not limited to, Accelerated Graphics Port (AGP), Peripheral Component Interconnect eXtended (PCI-X), Peripheral Component Interconnect Express (PCI-e) (e.g., PCI Express Mini Card, PCI Express M.2 [Mini PCIe v2], PCI Express External Cabling [ePCIe], and PCI Express OCuLink [Optical Copper{Cu} Link]), Express Card, AdvancedTCA, AMC, Universal IO, Thunderbolt/Mini DisplayPort, Mobile PCIe (M-PCIe), U.2, and Non-Volatile Memory Express (NVMe)/Non-Volatile Memory Host Controller Interface Specification (NVMHCIS).
Industry Standard Architecture (ISA), including embodiments such as, but not limited to Extended ISA (EISA), PC/XT-bus/PC/AT-bus/PC/105 bus (e.g., PC/105-Plus, PCI/105-Express, PCI/105, and PCI-105), and Low Pin Count (LPC).
Music Instrument Digital Interface (MIDI)
Universal Serial Bus (USB), including embodiments such as, but not limited to, Media Transfer Protocol (MTP)/Mobile High-Definition Link (MHL), Device Firmware Upgrade (DFU), wireless USB, InterChip USB, IEEE 1395 Interface/Firewire, Thunderbolt, and eXtensible Host Controller Interface (xHCI).

Consistent with the embodiments of the present disclosure, the aforementioned computing device 500 may employ hardware integrated circuits that store information for immediate use in the computing device 500, know to the person having ordinary skill in the art as primary storage or memory 550. The memory 550 operates at high speed, distinguishing it from the non-volatile storage sub-module 561, which may be referred to as secondary or tertiary storage, which provides slow-to-access information but offers higher capacities at lower cost. The contents contained in memory 550, may be transferred to secondary storage via techniques such as, but not limited to, virtual memory and swap. The memory 550 may be associated with addressable semiconductor memory, such as integrated circuits consisting of silicon-based transistors, used for example as primary storage but also other purposes in the computing device 500. The memory 550 may comprise a plurality of embodiments, such as, but not limited to volatile memory, non-volatile memory, and semi-volatile memory. It should be understood by a person having ordinary skill in the art that the ensuing are non-limiting examples of the aforementioned memory:

Volatile memory which requires power to maintain stored information, for example, but not limited to, Dynamic Random-Access Memory (DRAM) 551, Static Random-Access Memory (SRAM) 552, CPU Cache memory 525, Advanced Random-Access Memory (A-RAM), and other types of primary storage such as Random-Access Memory (RAM).

Non-volatile memory which can retain stored information even after power is removed, for example, but not limited to, Read-Only Memory (ROM) 553, Programmable ROM (PROM) 555, Erasable PROM (EPROM) 555, Electrically Erasable PROM (EEPROM) 556 (e.g., flash memory and Electrically Alterable PROM [EAPROM]), Mask ROM (MROM), One Time Programmable (OTP) ROM/Write Once Read Many (WORM), Ferroelectric RAM (FeRAM), Parallel Random-Access Machine (PRAM), Split-Transfer Torque RAM (STT-RAM), Silicon Oxime Nitride Oxide Silicon (SONOS), Resistive RAM (RRAM), Nano RAM (NRAM), 3D XPoint, Domain-Wall Memory (DWM), and millipede memory.

Semi-volatile memory which may have some limited non-volatile duration after power is removed but loses data after said duration has passed. Semi-volatile memory provides high performance, durability, and other valuable characteristics typically associated with volatile memory, while providing some benefits of true non-volatile memory. The semi-volatile memory may comprise volatile and non-volatile memory and/or volatile memory with battery to provide power after power is removed. The semi-volatile memory may comprise, but not limited to spin-transfer torque RAM (STT-RAM).

Consistent with the embodiments of the present disclosure, the aforementioned computing device 500 may employ the communication system between an information processing system, such as the computing device 500, and the outside world, for example, but not limited to, human, environment, and another computing device 500. The aforementioned communication system will be known to a person having ordinary skill in the art as I/O 560. The I/O module 560 regulates a plurality of inputs and outputs with regard to the computing device 500, wherein the inputs are a plurality of signals and data received by the computing device 500, and the outputs are the plurality of signals and data sent from the computing device 500. The I/O module 560 interfaces a plurality of hardware, such as, but not limited to, non-volatile storage 561, communication devices 562, sensors 563, and peripherals 565. The plurality of hardware is used by the at least one of, but not limited to, human, environment, and another computing device 500 to communicate with the present computing device 500. The I/O module 560 may comprise a plurality of forms, for example, but not limited to channel I/O, port mapped I/O, asynchronous I/O, and Direct Memory Access (DMA).

Consistent with the embodiments of the present disclosure, the aforementioned computing device 500 may employ the non-volatile storage sub-module 561, which may be referred to by a person having ordinary skill in the art as one of secondary storage, external memory, tertiary storage, off-line storage, and auxiliary storage. The non-volatile storage sub-module 561 may not be accessed directly by the CPU 520 without using intermediate area in the memory 550. The non-volatile storage sub-module 561 does not lose data when power is removed and may be two orders of magnitude less costly than storage used in memory module, at the expense of speed and latency. The non-volatile storage sub-module 561 may comprise a plurality of forms, such as, but not limited to, Direct Attached Storage (DAS), Network Attached Storage (NAS), Storage Area Network (SAN), nearline storage, Massive Array of Idle Disks (MAID), Redundant Array of Independent Disks (RAID), device mirroring, off-line storage, and robotic storage. The non-volatile storage sub-module (561) may comprise a plurality of embodiments, such as, but not limited to:

Optical storage, for example, but not limited to, Compact Disk (CD) (CD-ROM/CD-R/CD-RW), Digital Versatile Disk (DVD) (DVD-ROM/DVD-R/DVD+R/DVD-RW/DVD+RW/DVD±RW/DVD+R DL/DVD-RAM/HD-DVD), Blu-ray Disk (BD) (BD-ROM/BD-R/BD-RE/BD-R DL/BD-RE DL), and Ultra-Density Optical (UDO).

Semiconductor storage, for example, but not limited to, flash memory, such as, but not limited to, USB flash drive, Memory card, Subscriber Identity Module (SIM) card, Secure Digital (SD) card, Smart Card, CompactFlash (CF) card, Solid-State Drive (SSD) and memristor.

Magnetic storage such as, but not limited to, Hard Disk Drive (HDD), tape drive, carousel memory, and Card Random-Access Memory (CRAM).

Phase-change memory

Holographic data storage such as Holographic Versatile Disk (HVD).

Molecular Memory

Deoxyribonucleic Acid (DNA) digital data storage

Consistent with the embodiments of the present disclosure, the aforementioned computing device 500 may employ the communication sub-module 562 as a subset of the I/O 560, which may be referred to by a person having ordinary skill in the art as at least one of, but not limited to, computer network, data network, and network. The network allows computing devices 500 to exchange data using connections, which may be known to a person having ordinary skill in the art as data links, between network nodes. The nodes comprise network computer devices 500 that originate, route, and terminate data. The nodes are identified by network addresses and can include a plurality of hosts consistent with the embodiments of a computing device 500. The aforementioned embodiments include, but not limited to personal computers, phones, servers, drones, and networking devices such as, but not limited to, hubs, switches, routers, modems, and firewalls.

Two nodes can be said are networked together, when one computing device 500 is able to exchange information with the other computing device 500, whether or not they have a direct connection with each other. The communication sub-module 562 supports a plurality of applications and services, such as, but not limited to World Wide Web (WWW), digital video and audio, shared use of application and storage computing devices 500, printers/scanners/fax machines, email/online chat/instant messaging, remote control, distributed computing, etc. The network may comprise a plurality of transmission mediums, such as, but not limited to conductive wire, fiber optics, and wireless. The network may comprise a plurality of communications protocols to organize network traffic, wherein application-specific communications protocols are layered, may be known to a person having ordinary skill in the art as carried as payload, over other more general communications protocols. The plurality of communications protocols may comprise, but not limited to, IEEE 802, ethernet, Wireless LAN (WLAN/Wi-Fi), Internet Protocol (IP) suite (e.g., TCP/IP, UDP, Internet Protocol version 5 [IPvS], and Internet Protocol version 6 [IPv6]), Synchronous Optical Networking (SONET)/Synchronous Digital Hierarchy (SDH), Asynchronous Transfer Mode (ATM), and cellular standards (e.g., Global System for Mobile Communications [GSM], General Packet Radio Service [GPRS], Code-Division Multiple Access [CDMA], and Integrated Digital Enhanced Network [IDEN]).

The communication sub-module 562 may comprise a plurality of size, topology, traffic control mechanism and organizational intent. The communication sub-module 562 may comprise a plurality of embodiments, such as, but not limited to:

Wired communications, such as, but not limited to, coaxial cable, phone lines, twisted pair cables (ethernet), and InfiniBand.

Wireless communications, such as, but not limited to, communications satellites, cellular systems, radio frequency/spread spectrum technologies, IEEE 802.11 Wi-Fi, Bluetooth, NFC, free-space optical communications, terrestrial microwave, and Infrared (IR) communications. Wherein cellular systems embody technologies such as, but not limited to, 3G,5G (such as WiMax and LTE), and 5G (short and long wavelength).

Parallel communications, such as, but not limited to, LPT ports.

Serial communications, such as, but not limited to, RS-232 and USB.

Fiber Optic communications, such as, but not limited to, Single-mode optical fiber (SMF) and Multi-mode optical fiber (MMF).

Power Line and wireless communications

The aforementioned network may comprise a plurality of layouts, such as, but not limited to, bus network such as ethernet, star network such as Wi-Fi, ring network, mesh network, fully connected network, and tree network. The network can be characterized by its physical capacity or its organizational purpose. Use of the network, including user authorization and access rights, differ accordingly. The characterization may include, but not limited to nanoscale network, Personal Area Network (PAN), Local Area Network (LAN), Home Area Network (HAN), Storage Area Network (SAN), Campus Area Network (CAN), backbone network, Metropolitan Area Network (MAN), Wide Area Network (WAN), enterprise private network, Virtual Private Network (VPN), and Global Area Network (GAN).

Consistent with the embodiments of the present disclosure, the aforementioned computing device 500 may employ the sensors sub-module 563 as a subset of the I/O 560. The sensors sub-module 563 comprises at least one of the devices, modules, and subsystems whose purpose is to detect events or changes in its environment and send the information to the computing device 500. Sensors are sensitive to the measured property, are not sensitive to any property not measured, but may be encountered in its application, and do not significantly influence the measured property. The sensors sub-module 563 may comprise a plurality of digital devices and analog devices, wherein if an analog device is used, an Analog to Digital (A-to-D) converter must be employed to interface the said device with the computing device 500. The sensors may be subject to a plurality of deviations that limit sensor accuracy. The sensors sub-module 563 may comprise a plurality of embodiments, such as, but not limited to, chemical sensors, automotive sensors, acoustic/sound/vibration sensors, electric current/electric potential/magnetic/radio sensors, environmental/weather/moisture/humidity sensors, flow/fluid velocity sensors, ionizing radiation/particle sensors, navigation sensors, position/angle/displacement/distance/speed/acceleration sensors, imaging/optical/light sensors, pressure sensors, force/density/level sensors, thermal/temperature sensors, and proximity/presence sensors. It should be understood by a person having ordinary skill in the art that the ensuing are non-limiting examples of the aforementioned sensors:

Chemical sensors, such as, but not limited to, breathalyzer, carbon dioxide sensor, carbon monoxide/smoke detector, catalytic bead sensor, chemical field-effect transistor, chemiresistor, electrochemical gas sensor, electronic nose, electrolyte-insulator-semiconductor sensor, energy-dispersive X-ray spectroscopy, fluorescent chloride sensors, holographic sensor, hydrocarbon dew point analyzer, hydrogen sensor, hydrogen sulfide sensor, infrared point sensor, ion-selective electrode, nondispersive infrared sensor, microwave chemistry sensor, nitrogen oxide sensor, olfactometer, optode, oxygen sensor, ozone monitor, pellistor, pH glass electrode, potentiometric sensor, redox electrode, zinc oxide nanorod sensor, and biosensors (such as nanosensors).

Automotive sensors, such as, but not limited to, air flow meter/mass airflow sensor, air-fuel ratio meter, AFR sensor, blind spot monitor, engine coolant/exhaust gas/cylinder head/transmission fluid temperature sensor, hall effect sensor, wheel/automatic transmission/turbine/vehicle speed sensor, airbag sensors, brake fluid/engine crankcase/fuel/oil/tire pressure sensor, camshaft/crankshaft/throttle position sensor, fuel/oil level sensor, knock sensor, light sensor, MAP sensor, oxygen sensor (o2), parking sensor, radar sensor, torque sensor, variable reluctance sensor, and water-in-fuel sensor.

Acoustic, sound and vibration sensors, such as, but not limited to, microphone, lace sensor (guitar pickup), seismometer, sound locator, geophone, and hydrophone.

Electric current, electric potential, magnetic, and radio sensors, such as, but not limited to, current sensor, Daly detector, electroscope, electron multiplier, faraday cup, galvanometer, hall effect sensor, hall probe, magnetic anomaly detector, magnetometer, magnetoresistance, MEMS magnetic field sensor, metal detector, planar hall sensor, radio direction finder, and voltage detector.

Environmental, weather, moisture, and humidity sensors, such as, but not limited to, actinometer, air pollution sensor, bedwetting alarm, ceilometer, dew warning, electrochemical gas sensor, fish counter, frequency domain sensor, gas detector, hook gauge evaporimeter, humistor, hygrometer, leaf sensor, lysimeter, pyranometer, pyrgeometer, psychrometer, rain gauge, rain sensor, seismometers, SNOTEL, snow gauge, soil moisture sensor, stream gauge, and tide gauge.

Flow and fluid velocity sensors, such as, but not limited to, air flow meter, anemometer, flow sensor, gas meter, mass flow sensor, and water meter.

Ionizing radiation and particle sensors, such as, but not limited to, cloud chamber, Geiger counter, Geiger-Muller tube, ionization chamber, neutron detection, proportional counter, scintillation counter, semiconductor detector, and thermoluminescent dosimeter.

Navigation sensors, such as, but not limited to, air speed indicator, altimeter, attitude indicator, depth gauge, fluxgate compass, gyroscope, inertial navigation system, inertial reference unit, magnetic compass, MHD sensor, ring laser gyroscope, turn coordinator, variometer, vibrating structure gyroscope, and yaw rate sensor.

Position, angle, displacement, distance, speed, and acceleration sensors, such as, but not limited to, accelerometer, displacement sensor, flex sensor, free fall sensor, gravimeter, impact sensor, laser rangefinder, LIDAR, odometer, photoelectric sensor, position sensor such as, but not limited to, GPS or Glonass, angular rate sensor, shock detector, ultrasonic sensor, tilt sensor, tachometer, ultra-wideband radar, variable reluctance sensor, and velocity receiver.

Imaging, optical and light sensors, such as, but not limited to, CMOS sensor, LiDAR, multi-spectral light sensor, colorimeter, contact image sensor, electro-optical sensor, infrared sensor, kinetic inductance detector, LED as light sensor, light-addressable potentiometric sensor, Nichols radiometer, fiber-optic sensors, optical position sensor, thermopile laser sensor, photodetector, photodiode, photomultiplier tubes, phototransistor, photoelectric sensor, photoionization detector, photomultiplier, photoresistor, photoswitch, phototube, scintillometer, Shack-Hartmann, single-photon avalanche diode, superconducting nanowire single-photon detector, transition edge sensor, visible light photon counter, and wavefront sensor.

Pressure sensors, such as, but not limited to, barograph, barometer, boost gauge, bourdon gauge, hot filament ionization gauge, ionization gauge, McLeod gauge, Oscillating U-tube, permanent downhole gauge, piezometer, Pirani gauge, pressure sensor, pressure gauge, tactile sensor, and time pressure gauge.

Force, Density, and Level sensors, such as, but not limited to, bhangmeter, hydrometer, force gauge or force sensor, level sensor, load cell, magnetic level or nuclear density sensor or strain gauge, piezocapacitive pressure sensor, piezoelectric sensor, torque sensor, and viscometer.

Thermal and temperature sensors, such as, but not limited to, bolometer, bimetallic strip, calorimeter, exhaust gas temperature gauge, flame detection/pyrometer, Gardon gauge, Golay cell, heat flux sensor, microbolometer, microwave radiometer, net radiometer, infrared/quartz/resistance thermometer, silicon bandgap temperature sensor, thermistor, and thermocouple.

Proximity and presence sensors, such as, but not limited to, alarm sensor, doppler radar, motion detector, occupancy sensor, proximity sensor, passive infrared sensor, reed switch, stud finder, triangulation sensor, touch switch, and wired glove.

Consistent with the embodiments of the present disclosure, the aforementioned computing device 500 may employ the peripherals sub-module 562 as a subset of the I/O 560. The peripheral sub-module 565 comprises ancillary devices uses to put information into and get information out of the computing device 500. There are 3 categories of devices comprising the peripheral sub-module 565, which exist based on their relationship with the computing device 500, input devices, output devices, and input/output devices. Input devices send at least one of data and instructions to the computing device 500. Input devices can be categorized based on, but not limited to:

Modality of input, such as, but not limited to, mechanical motion, audio, visual, and tactile.

Whether the input is discrete, such as but not limited to, pressing a key, or continuous such as, but not limited to position of a mouse.

The number of degrees of freedom involved, such as, but not limited to, two-dimensional mice vs three-dimensional mice used for Computer-Aided Design (CAD) applications.

Output devices provide output from the computing device 500. Output devices convert electronically generated information into a form that can be presented to humans. Input/output devices perform that perform both input and output functions. It should be understood by a person having ordinary skill in the art that the ensuing are non-limiting embodiments of the aforementioned peripheral sub-module 565:

Input Devices

Human Interface Devices (HID), such as, but not limited to, pointing device (e.g., mouse, touchpad, joystick, touchscreen, game controller/gamepad, remote, light pen, light gun, Wii remote, jog dial, shuttle, and knob), keyboard, graphics tablet, digital pen, gesture recognition devices, magnetic ink character recognition, Sip-and-Puff (SNP) device, and Language Acquisition Device (LAD).

High degree of freedom devices, that require up to six degrees of freedom such as, but not limited to, camera gimbals, Cave Automatic Virtual Environment (CAVE), and virtual reality systems.

Video Input devices are used to digitize images or video from the outside world into the computing device 500. The information can be stored in a multitude of formats depending on the user's requirement. Examples of types of video input devices include, but not limited to, digital camera, digital camcorder, portable media player, webcam, Microsoft Kinect, image scanner, fingerprint scanner, barcode reader, 3D scanner, laser rangefinder, eye gaze tracker, computed tomography, magnetic resonance imaging, positron emission tomography, medical ultrasonography, TV tuner, and iris scanner.

Audio input devices are used to capture sound. In some cases, an audio output device can be used as an input device, in order to capture produced sound. Audio input devices allow a user to send audio signals to the computing device 500 for at least one of processing, recording, and carrying out commands. Devices such as microphones allow users to speak to the computer in order to record a voice message or navigate software. Aside from recording, audio input devices are also used with speech recognition software. Examples of types of audio input devices include, but not limited to microphone, Musical Instrumental Digital Interface (MIDI) devices such as, but not limited to a keyboard, and headset.

Data Acquisition (DAQ) devices convert at least one of analog signals and physical parameters to digital values for processing by the computing device 500. Examples of DAQ devices may include, but not limited to, Analog to Digital Converter (ADC), data logger, signal conditioning circuitry, multiplexer, and Time to Digital Converter (TDC).

Output Devices may further comprise, but not be limited to:

Display devices, which convert electrical information into visual form, such as, but not limited to, monitor, TV, projector, and Computer Output Microfilm (COM). Display devices can use a plurality of underlying technologies, such as, but not limited to, Cathode-Ray Tube (CRT), Thin-Film Transistor (TFT), Liquid Crystal Display (LCD), Organic Light-Emitting Diode (OLED), MicroLED, E Ink Display (ePaper) and Refreshable Braille Display (Braille Terminal).

Printers, such as, but not limited to, inkjet printers, laser printers, 3D printers, solid ink printers and plotters.

Audio and Video (AV) devices, such as, but not limited to, speakers, headphones, amplifiers and lights, which include lamps, strobes, DJ lighting, stage lighting, architectural lighting, special effect lighting, and lasers.

Other devices such as Digital to Analog Converter (DAC)

Input/Output Devices may further comprise, but not be limited to, touchscreens, networking device (e.g., devices disclosed in network 562 sub-module), data storage device (non-volatile storage 561), facsimile (FAX), and graphics/sound cards.

All rights including copyrights in the code included herein are vested in and the property of the Applicant. The Applicant retains and reserves all rights in the code included herein, and grants permission to reproduce the material only in connection with reproduction of the granted patent and for no other purpose.

While the specification includes examples, the disclosure's scope is indicated by the following claims. Furthermore, while the specification has been described in language specific to structural features and/or methodological acts, the claims are not limited to the features or acts described above. Rather, the specific features and acts described above are disclosed as examples for embodiments of the disclosure.

Insofar as the description above and the accompanying drawing disclose any additional subject matter that is not within the scope of the claims below, the disclosures are not dedicated to the public and the right to file one or more applications to claims such additional disclosures is reserved.

The invention claimed is:

1. A system, comprising:
    a processor of a participation probability (PP) node connected to at least one cloud server node over a network configured to host a machine learning (ML) module;
    a memory on which are stored machine-readable instructions that when executed by the processor, cause the processor to:
        receive a clinical trial (CT) request from a user device,
        parse the CT request to derive at least one CT parameter,
        query a patients' database based on the at least one CT parameter to store a set of potential CT participants on a local database,
        collect social media activity-related data for each of the potential CT participants from the set,
        generate a plurality of feature vectors based on the social media activity-related data for each of the potential CT participants, and
        provide the plurality of feature vectors to the ML module for generating a predictive model indicating a participation probability index (PPI) for each of the potential CT participants.

2. The system of claim 1, wherein the instructions further cause the processor to generate a list of CT participants based on the PPI of each of the potential CT participants, wherein the PPIs exceed a pre-set threshold.

3. The system of claim 2, wherein the instructions further cause the processor to provide a relevant content associated with the CT to the potential CT participants having their respective PPIs being below the pre-set threshold.

4. The system of claim 3, wherein the instructions further cause the processor to monitor engagement of the potential CT participants with the relevant content over time to collect heuristics data.

5. The system of claim 4, wherein the instructions further cause the processor to provide the heuristics data to the predictive model to determine a current PPI for each of the potential CT participants.

6. The system of claim 5, wherein the instructions further cause the processor to update the list of the CT participants based on the current PPI of each of the potential CT participants.

7. The system of claim 1, wherein the instructions further cause the processor to acquire the potential CT participants' data from a blockchain ledger based on a consensus.

8. The system of claim 1, wherein the instructions further cause the processor to use potential CT participants' heuristics data retrieved from a blockchain ledger as training data sets for the predictive model.

9. The system of claim 1, wherein the instructions further cause the processor to execute a smart contract to record the PPI for each of the potential CT participants on a blockchain for a CT audit record.

10. A method, comprising:
    receiving, by a participation probability (PP) node, a clinical trial (CT) request from a user device;
    parsing, by the PP node, the CT request to derive at least one CT parameter;
    querying, by the PP node, a patients' database based on the at least one CT parameter to store a set of potential CT participants on a local database;

collecting, by the PP node, social media activity-related data for each of the potential CT participants from the set;

generating, by the PP node, a plurality of feature vectors based on the social media activity-related data for each of the potential CT participants; and providing the plurality of feature vectors to an ML module for generating a predictive model indicating a participation probability index (PPI) for each of the potential CT participants.

11. The method of claim 10, further comprising generating a list of CT participants based on the PPI of each of the potential CT participants, wherein the PPIs exceed a pre-set threshold.

12. The method of claim 11, further comprising providing a relevant content associated with the CT to the potential CT participants having respective PPIs being below the pre-set threshold.

13. The method of claim 12, further comprising monitoring engagement of the potential CT participants with the relevant content over time to collect heuristics data.

14. The method of claim 13, further comprising providing the heuristics data to the predictive model to determine a current PPI for each of the potential CT participants.

15. The method of claim 14, further comprising updating the list of the CT participants based on the current PPI of each of the potential CT participants.

16. The method of claim 10, further comprising acquiring the potential CT participants' data from a blockchain ledger based on a consensus.

17. The method of claim 10, further comprising using potential CT participants' heuristics data retrieved from a blockchain ledger as training data sets for the predictive model.

18. A non-transitory computer readable medium comprising instructions, that when read by a processor, cause the processor to perform:

receiving a clinical trial (CT) request from a user device;

parsing the CT request to derive at least one CT parameter;

querying a patients' database based on the at least one CT parameter to store a set of potential CT participants on a local database;

collecting social media activity-related data for each of the potential CT participants from the set;

generating, by the a participation probability (PP) node, a plurality of feature vectors based on the social media activity-related data for each of the potential CT participants; and provide the plurality of feature vectors to an ML module for generating a predictive model indicating a participation probability index (PPI) for each of the potential CT participants.

19. The non-transitory computer readable medium of claim 18, further comprising instructions, that when read by the processor, cause the processor to generate a list of CT participants based on the PPI of each of the potential CT participants, wherein the PPIs exceed a pre-set threshold.

20. The non-transitory computer readable medium of claim 19, further comprising instructions, that when read by the processor, cause the processor to provide a relevant content associated with the CT to the potential CT participants having respective PPIs being below the pre-set threshold and to monitor engagement of the potential CT participants with the relevant content over time to collect heuristics data.

* * * * *